US00PP34690P2

(12) United States Plant Patent
Beekenkamp

(10) Patent No.: US PP34,690 P2
(45) Date of Patent: Oct. 25, 2022

(54) ***DAHLIA* PLANT NAMED 'BKDAFRW'**

(50) Latin Name: *Dahlia hybrida*
Varietal Denomination: 'BKDAFRW'

(71) Applicant: BEEKENKAMP PLANTS B.V., Maasdijk (NL)

(72) Inventor: Annie Cornelia Beekenkamp, Maasdijk (NL)

(73) Assignee: BEEKENKAMP PLANTS B.V., Maasdijk (NL)

( * ) Notice: Subject to any disclaimer, the term of this patent is extended or adjusted under 35 U.S.C. 154(b) by 0 days.

(21) Appl. No.: 17/709,961

(22) Filed: Mar. 31, 2022

(51) Int. Cl.
*A01H 5/02* (2018.01)
*A01H 6/14* (2018.01)

(52) U.S. Cl.
USPC ..... Plt./321

(58) Field of Classification Search
USPC ..... Plt./263.1, 321
See application file for complete search history.

*Primary Examiner* — Susan McCormick Ewoldt
*Assistant Examiner* — Karen M Redden
(74) *Attorney, Agent, or Firm* — C. Anne Whealy

(57) ABSTRACT

A new and distinct cultivar of *Dahlia* plant named 'BKDAFRW', characterized by its broadly upright plant habit; vigorous growth habit; freely branching habit; dense and bushy growth habit; dark green-colored leaves; freely and continuously flowering habit; large, decorative type inflorescences with red and white bi-colored ray florets; and good garden performance.

2 Drawing Sheets

Figure 1:
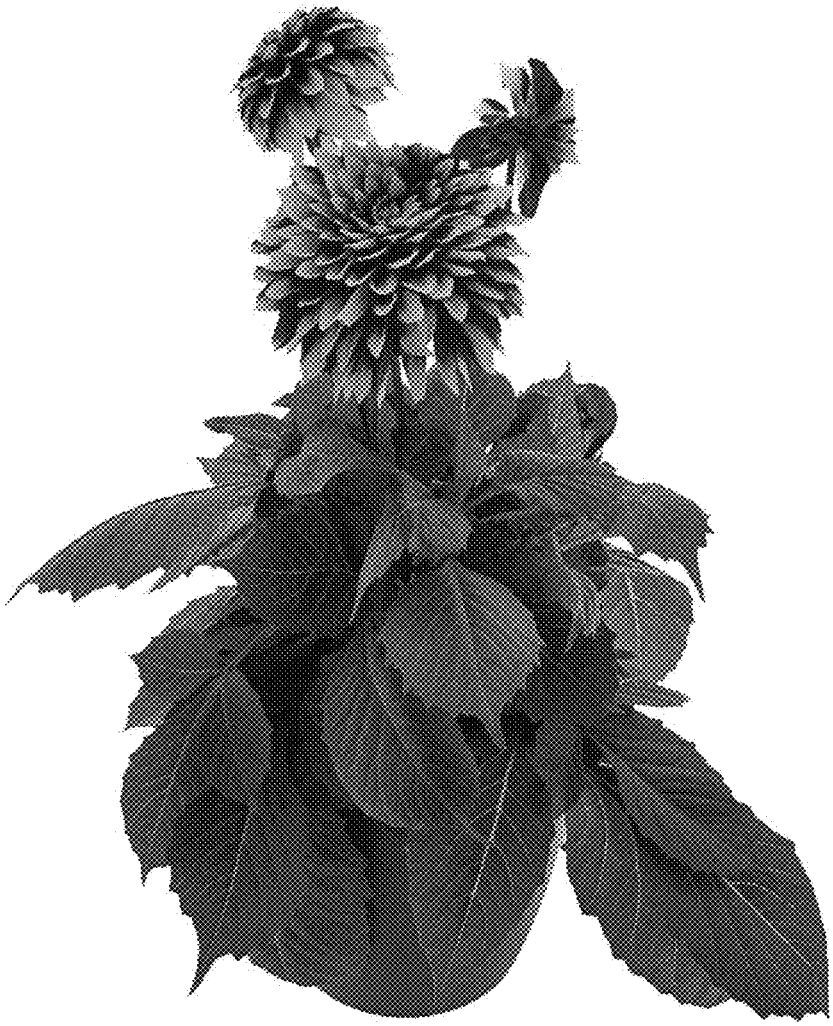

Botanical designation: *Dahlia hybrida.*
Cultivar denomination: 'BKDAFRW'.

STATEMENT REGARDING PRIOR DISCLOSURES BY INVENTOR/APPLICANT and ASSIGNEE

An European Community Plant Breeder's Rights application for the instant plant was filed by the Applicant/Assignee of the instant application, Beekenkamp Plants B.V. of Maasdijk, The Netherlands on Jan. 31, 2022, application number 2022/0285. Foreign priority is not claimed to this European Community Plant Breeder's Rights application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Dahlia* plant, botanically known as *Dahlia hybrida* and hereinafter referred to by the name 'BKDAFRW'.

The new *Dahlia* plant is a product of a planned breeding program conducted by the Inventor in Maasdijk, The Netherlands. The objective of the breeding program is to create new freely branching container *Dahlia* plants with large inflorescences and attractive ray floret coloration.

The new *Dahlia* plant originated from an open-pollination in September, 2015 in Maasdijk, The Netherlands of a proprietary selection of *Dahlia hybrida* identified as code number 15-0124-98, as the female, or seed, parent with an unknown selection of *Dahlia hybrida* as the male, or pollen, parent. The new *Dahlia* plant was discovered and selected by the Inventor as a single flowering plant from within the progeny of the stated open-pollination in a controlled greenhouse environment in Maasdijk, The Netherlands in November, 2016.

Asexual reproduction of the new *Dahlia* plant by terminal cuttings in a controlled greenhouse environment in Maasdijk, The Netherlands since February, 2017 has shown that the unique features of this new *Dahlia* plant are stable and reproduced true to type in successive generations.

SUMMARY OF THE INVENTION

Plants of the new *Dahlia* have not been observed under all possible combinations of environmental conditions and cultural conditions. The phenotype may vary somewhat with variations in environmental conditions such as temperature and light intensity, without, however, any variance in genotype.

The following traits have been repeatedly observed and are determined to be the unique characteristics of 'BKDAFRW'. These characteristics in combination distinguish 'BKDAFRW' as a new and distinct *Dahlia* plant:

1. Broadly upright plant habit.
2. Vigorous growth habit.
3. Freely branching habit; dense and bushy growth habit.
4. Dark green-colored leaves.
5. Freely and continuously flowering habit.
6. Large, decorative type inflorescences with red and white bi-colored ray florets.
7. Good garden performance.

Plants of the new *Dahlia* differ primarily from plants of the female parent selection in inflorescence form as plants of the new *Dahlia* have double type inflorescences whereas plants of the female parent selection have semi-double type inflorescences. In addition, ray florets of plants of the new *Dahlia* are red and white bi-colored whereas ray florets of plants of the female parent selection are pink and white bi-colored.

Plants of the new *Dahlia* can be compared to plants of *Dahlia hybrida* 'BKDAMAGRB', disclosed in U.S. Plant Pat. No. 30,691. In side-by-side comparisons, plants of the new *Dahlia* differ primarily from plants of 'BKDAMAGRB' in inflorescence size as plants of the new *Dahlia* have smaller inflorescences than plants of 'BKDAMAGRB'. In addition, ray florets of plants of the new *Dahlia* are red and white bi-colored whereas ray florets of plants of 'BKDAMAGRB' are red purple and white bi-colored.

BRIEF DESCRIPTION OF THE PHOTOGRAPHS

The accompanying photographs illustrate the overall appearance of the new *Dahlia* plant showing the colors as true as it is reasonably possible to obtain in colored reproductions of this type. Colors in the photographs may differ slightly from the color values cited in the detailed botanical description which accurately describe the colors of the new *Dahlia* plant.

The photograph on the first sheet (FIG. 1) is a side perspective view of a typical flowering plant of 'BKDAFRW' grown in a container.

Figure 2:
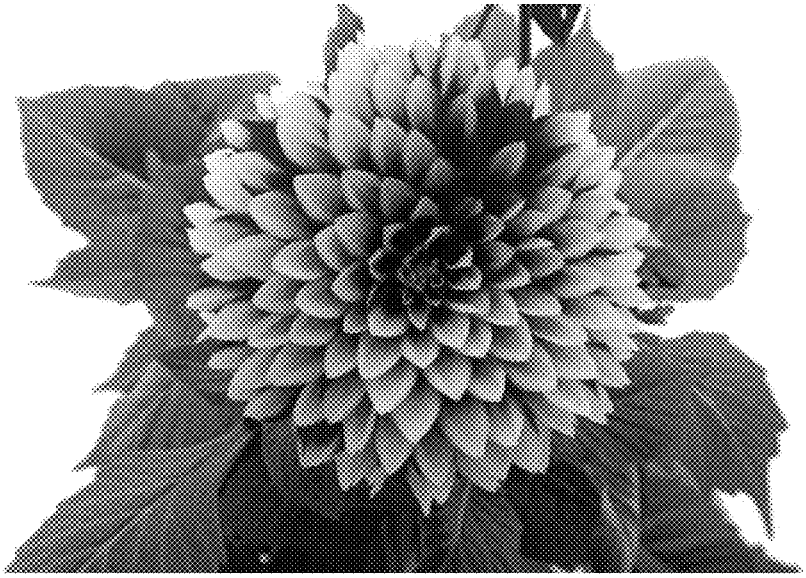

The photograph on the second sheet (FIG. 2) is a close-up view of a typical inflorescence and leaves of 'BKDAFRW'.

DETAILED BOTANICAL DESCRIPTION

The aforementioned photographs and the following observations and measurements describe plants grown during the winter in 15-cm containers in a glass-covered greenhouse in Maasdijk, The Netherlands and under cultural practices typical of commercial *Dahlia* production. During the production of the plants, day and night temperatures ranged from 17° C. to 19° C. Plants were pinched one time and were eight weeks from planting rooted cuttings when the photographs and description were taken. In the following description, color references are made to The Royal Horticultural Society Colour Chart, 2015 Edition, except where general terms of ordinary dictionary significance are used.

Botanical classification: *Dahlia hybrida* 'BKDAFRW'.

Parentage:

- *Female, or seed, parent*.—Proprietary selection of *Dahlia hybrida* identified as code number 15-0124-98, not patented.
- *Male, or pollen, parent*.—Unknown selection of *Dahlia hybrida*, not patented.

Propagation:

- *Type*.—By terminal cuttings.
- *Time to initiate roots, summer*.—About 16 days at temperatures ranging from 18° C. to 21° C.
- *Time to initiate roots, winter*.—About 19 days at temperatures about 21° C.
- *Time to produce a rooted young plant, summer*.—About 21 days at temperatures ranging from 18° C. to 21° C.
- *Time to produce a rooted young plant, winter*.—About 23 days at temperatures ranging from 19° C. to 21° C.
- *Root description*.—Medium in thickness, fibrous; typically white in color, actual color of the roots is dependent on substrate composition, water quality, fertilizers, substrate temperature and physiological age of roots; tuber development has not been observed on plants of the new *Dahlia*.
- *Rooting habit*.—Moderately freely branching; medium density.

Plant description:

- *Plant and growth habit*.—Broadly upright plant habit; overall plant shape, broadly ovate to broadly oblong with inflorescences held above the foliar plane on strong peduncles; vigorous growth habit and moderate growth rate.
- *Plant height, soil level to top of foliar plane*.—About 22.2 cm.
- *Plant height, soil level to top of floral plane*.—About 34.5 cm.
- *Plant diameter or spread*.—About 34.7 cm.
- *Lateral branches*.—Quantity: Freely basal branching habit with about nine lateral branches developing per plant; bushy and dense growth habit; pinching is not required but will improve branching habit. Length: About 12.6 cm. Diameter: About 5 mm. Internode length: About 5 cm. Aspect: Primary branches are about 10° from vertical; secondary branches are about 30° from primary branch axis. Strength: Moderately strong to strong. Texture and luster: Smooth, glabrous; glossy. Color, developing: Close to 146A strongly tinged with close to N199B. Color, developed: Close to 146A to 146B slightly tinged with close to N199B.

Leaf & leaflet description:

- *Arrangement*.—Leaves opposite; single and compound with typically three leaflets.
- *Length, single leaves*.—About 19.3 cm.
- *Width, single leaves*.—About 10.4 cm.
- *Length, compound leaves*.—About 19.6 cm.
- *Width, compound leaves*.—About 22.6 cm.
- *Length, terminal leaflets*.—About 14.2 cm.
- *Width, terminal leaflets*.—About 8 cm.
- *Length, lateral leaflets*.—About 11.7 cm.
- *Width, lateral leaflets*.—About 6.4 cm.
- *Shape, single leaves*.—Broadly elliptic.
- *Shape, compound leaves*.—Broadly ovate in overall outline.
- *Shape, leaflets*.—Broadly ovate to broadly elliptic.
- *Apex, leaves and leaflets*.—Apiculate.
- *Base, leaves and leaflets*.—Short attenuate to long attenuate.
- *Margin, leaves and leaflets*.—Coarsely dentate.
- *Venation pattern, leaves and leaflets*.—Pinnate.
- *Texture and luster, leaves and leaflets, upper surface*.—Smooth, glabrous; slightly glossy.
- *Texture and luster, leaves and leaflets, lower surface*.—Smooth, glabrous; matte.
- *Color*.—Developing leaves and leaflets, upper surface: Close to 137B. Developing leaves and leaflets, lower surface: Close to 147B. Fully expanded leaves and leaflets, upper surface: Close to NN137A; venation, close to 146B to 146C, proximally, strongly tinged with close to 178A. Fully expanded leaves and leaflets, lower surface: Close to 191A; venation, close to 148B, proximally, slightly tinged with close to 176B.
- *Petioles*.—Length, single leaves: About 5.9 cm. Diameter, single leaves: About 4 mm by 4.5 mm. Length, compound leaves: About 4.7 cm. Diameter, compound leaves: About 4 mm by 5 mm. Strength, single and compound leaves: Moderately strong. Texture and luster, single and compound leaves, upper and lower surfaces: Smooth, glabrous; moderately glossy. Color, single and compound leaves, upper surface: Close to 177B to 177C; at proximal and distal ends, strongly tinged with close to 178A to darker than 178A; towards the margins, close to 146A. Color, single and compound leaves, lower surface: Close to 148A and 148B.

Inflorescence description:

*Appearance and arrangement*.—Decorative type inflorescences with ray and disc florets forming acropetally on a receptacle; inflorescences positioned above and beyond the foliar plane on strong peduncles; inflorescences face mostly upright; freely flowering habit with about 30 inflorescences developing per plant.

*Fragrance*.—None detected.

*Flowering response and flowering period*.—Early flowering habit, plants begin flowering about 56 days after planting; plants flower continuously during the autumn into the winter in The Netherlands.

*Post-production longevity*.—Plants maintain good substance for about six months; inflorescences persistent.

*Inflorescence buds*.—Height: About 2.4 cm. Diameter: About 3.3 cm. Shape: Flattened globular; involucral bracts moderately reflexed. Texture and luster: Smooth, glabrous; glossy. Color: Close to 144A moderately tinged with close to 37A and 37B; towards the apex, close to 144C and 145A.

*Inflorescence size*.—Diameter: About 11.2 cm. Depth (height): About 8.6 cm. Disc diameter: About 1.1 cm; typically inconspicuous.

*Receptacles*.—Height: About 7 mm. Diameter: About 1.1 cm. Shape: Lunate. Color: Close to 145B.

*Ray florets*.—Quantity per inflorescence and arrangement: About 180 arranged in about eight whorls. Length: About 4.9 cm; varying between 4 cm and 5.4 cm. Width: About 2.2 cm; varying between 2 cm and 2.6 cm. Shape: Obovate; strongly carinate. Apex: Acute. Base: Cuneate. Margin: Entire, not undulate. Aspect: Upright to horizontal; reflexing with subsequent development. Texture and luster, upper surface: Smooth, glabrous; velvety; matte. Texture and luster, lower surface: Smooth, glabrous; slightly velvety; matte. Color: When opening, upper surface: Proximally, close to a blend of 59A and 187A to slightly darker than 187A; distally, close to 65B and 75C. When opening, lower surface: Proximally, close to 60A; distally, close to 65B and 75C. Fully opened, upper surface: Proximally, close to N45A to N45B; distally, close to N155B to lighter than N155B; venation, similar to lamina colors; color does not change with subsequent development. Fully opened, lower surface: Proximally, close to N45C; distally, close to N155B to lighter than N155B; venation, close to N170D; color does not change with subsequent development.

*Disc florets*.—Quantity per inflorescence and arrangement: About 40 massed at the center of the inflorescence in about four spiral whorls; typically inconspicuous. Length: About 1.5 cm. Diameter: About 5 mm Shape: Tubular, elongated; lower 80% fused and upper 20% free; apices, acute and reflexed. Texture and luster, inner and outer surfaces: Smooth, glabrous; glossy. Color, when opening, inner and outer surfaces: Apex: Close to 15C and 15D. Mid-section and base: Close to 150D. Color, fully opened, inner and outer surfaces: Apex: Close to 15C. Mid-section and base: Close to 150D.

*Phyllaries*.—Quantity per inflorescence and arrangement: About seven to nine in a single whorl. Length: About 2.5 cm. Width: About 7 mm. Shape: Oblanceolate; strongly carinate towards the base. Apex: Acute. Base: Cuneate. Margin: Entire. Texture and luster, upper and lower surfaces: Smooth, glabrous; glossy. Color, upper surface: Close to NN137B; venation, close to NN137B. Color, lower surface: Close to 137B; venation, close to NN137A.

*Peduncles*.—Length, terminal peduncle: About 20.3 cm. Diameter, terminal peduncle: About 4 mm. Strength: Strong. Aspect: Mostly upright. Texture and luster: Smooth, glabrous; moderately glossy. Color: Close to a blend of N199B and 200C.

*Reproductive organs*.—Androecium, present on disc florets only: Quantity per floret: About five. Filament length: About 6 mm. Filament color: Close to 157D. Anther size: About 4 mm by 0.5 mm. Anther shape: Narrowly oblong. Anther color: Close to 15B. Pollen amount: Abundant. Pollen color: Close to 24A. Gynoecium, present on disc florets only: Quantity per floret: One. Pistil length: About 1.3 cm. Style length: About 1 cm. Style color: Close to 157D. Stigma diameter: About 5 mm. Stigma shape: Cleft. Stigma color: Close to 17A. Ovary color: Close to 145D. Seeds and fruits: To date, seed and fruit development have not been observed on plants of the new *Dahlia*.

Pathogen & pest resistance: To date, plants of the new *Dahlia* have not been observed to be resistant to pathogens and pests common to *Dahlia* plants.

Temperature tolerance: Plants of the new *Dahlia* have been observed to tolerate high temperatures of about 35° C. and to be suitable for USDA Hardiness Zones 9 to 11.

It is claimed:

1. A new and distinct *Dahlia* plant named 'BKDAFRW' as illustrated and described.

* * * * *